(12) United States Patent
Campbell

(10) Patent No.: US 12,215,125 B2
(45) Date of Patent: Feb. 4, 2025

(54) METHOD FOR SPRAY DRYING D-TAGATOSE

(71) Applicant: University of Kentucky Research Foundation, Lexington, KY (US)

(72) Inventor: Heather R. Campbell, Jackson, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 18/244,136

(22) Filed: Sep. 8, 2023

(65) Prior Publication Data

US 2024/0002421 A1 Jan. 4, 2024

Related U.S. Application Data

(62) Division of application No. 17/480,320, filed on Sep. 21, 2021, now Pat. No. 11,795,189.

(60) Provisional application No. 63/080,905, filed on Sep. 21, 2020.

(51) Int. Cl.
  *C07H 3/02* (2006.01)
(52) U.S. Cl.
  CPC ...................................... *C07H 3/02* (2013.01)
(58) Field of Classification Search
  CPC ...... C07H 3/02; A61K 9/1623; A61K 9/1635; A61K 9/1652; A61K 9/1694; A23L 33/125; C13K 13/00; B01J 2/04
  USPC .......................................................... 127/34
  See application file for complete search history.

(56) References Cited

U.S. PATENT DOCUMENTS

| 4,786,722 A | 11/1988 | Zehner |
| 2006/0040023 A1 | 2/2006 | Zeller |
| 2015/0290211 A1 | 10/2015 | Bosse |
| 2016/0015792 A1 | 1/2016 | Hendricus van Pinxteren |
| 2021/0244057 A1 | 8/2021 | Kim |

FOREIGN PATENT DOCUMENTS

| CN | 104739848 A | 7/2015 |
| WO | WO2020005021 A1 | 1/2020 |

OTHER PUBLICATIONS

Mehrotra, 1.07 Powder Processing and Green Shaping, 2014, Comprehensive Hard Materials, vol. 1, pp. 213-235 (Year: 2014).*
Anandharamakrishnan et al., Spray Drying Techniques for Food Ingredient Encapsulation, 2015, Wiley-Blackwell, pp. 1-36 (Year: 2015).*

(Continued)

*Primary Examiner* — Coris Fung
*Assistant Examiner* — Ritu S Shirali
(74) *Attorney, Agent, or Firm* — Stites & Harbison PLLC; Warren D. Schickli

(57) ABSTRACT

A D-tagatose spray-drying feed formulation is a mixture of D-tagatose and a functional excipient co-dissolved in a solvent to produce a excipient/D-tagatose composite having a glass transition temperature of greater than 30° C. A method of spray-drying D-tagatose includes the steps of (a) preparing the D-tagatose spray-drying formulation, (b) atomizing the D-tagatose spray-drying formulation in a drying chamber containing a hot inert processing gas and evaporating droplets to produce solid particles of excipient/D-tagatose composite and (c) separating and collecting the solid particles of excipient/D-tagatose composite from the processing gas.

10 Claims, 7 Drawing Sheets

(56) References Cited

OTHER PUBLICATIONS

Muzaffar, et al., Stickiness Problem Associated with Spray Drying of Sugar and Acid Rich Foods: A Mini Review, J Nutr Food Sci 2015, S12:003.

Roe, et al., Glass Transition and Crystallization of Amorphous Trehalose-sucrose Mixures, International Journal of Food Properties, 8: 559-574, 2005.

Kawai, et al., Maillard Reaction Rate in Various Glassy Matrices, Biosci. Biotechnol. Biochem., 68 (11), 2285-2288, 2004.

Howes, et al., Characterization of the Surface Stickiness of Fructose—Maltodextrin Solutions During Drying, Drying Technology vol. 21, No. 1, pp. 17-34, 2003.

Hugo, et al., Selection of excipient, solvent and packaging to optimize the performance of spray-dried formulations: case example fenofibrate, Drug Development and Industrial Pharmacy, 2013; 39(2): 402-412.

Bhandari, et al., Problems Associated Witb Spray Drying of Sugar-Rice Foods, Drying Technology. 15(2), 671-684 (1997).

Synonyms: Hydromellose [online], [retrieved on May 5, 2023]. Retrieved from the internet: < URL: https://www.synonyms.com/synonym/hypromellose > (Year: 2023).

NIH: Hypromellose acetate succinate [online], [retrieved on May 5, 2023]. Retrieved from the internet:< URL: https://pubchem .ncbi .nlm .nih .gov/compound/Hypromellose-acetate-succinate > (Year: 2023).

Machine translation of CN 104739848 A originally published Jul. 2015 to Bai et al. (Year: 2015).

\* cited by examiner

A = Target Tg for effective spray-drying
B = Measured Tg of pure D-tagatose

METHOD FOR SPRAY DRYING D-TAGATOSE

RELATED APPLICATIONS

This application is a division of prior U.S. patent application Ser. No. 17/480,320, filed on Sep. 21, 2021, which claims priority to U.S. provisional Patent Application Ser. No. 63/080,905, filed on Sep. 21, 2020, both of which is are hereby incorporated in their entirety by reference.

This application claims priority to U.S. Provisional Patent Application Ser. No. 63/080,905, filed on Sep. 21, 2020, which is hereby incorporated in its entirety by reference.

TECHNICAL FIELD

This document relates generally to the production of D-tagatose and, more particularly, to a new and improved method for producing D-tagatose by spray drying.

BACKGROUND

Sugar is commonly used in many industries, including the food and pharmaceutical industries. Food industries utilize sugar's sweet taste for flavor enhancement. In fact, sugar was estimated to be in 74% of all packaged foods between 2005 and 2009. Furthermore, sugar compounds such as lactose, trehalose, and mannitol commonly are used as functional excipients in the pharmaceutical arena as bulking agents, agents to add consistency to tablets, and to improve the taste of unpleasant-tasting active pharmaceutical ingredients (APIs) among other functions.

The use and applicability of sugars are significant and universal but come with potential drawbacks. Although it is difficult to single out a specific sugar, it has been suggested that excess sugar consumption has been linked to several diseases such as cardiovascular disease, obesity, and type 2 diabetes. Diabetes alone was estimated to cost Americans more than $327 billion in 2017. Therefore, it is critical to find healthier alternatives without compromising the functionality and sweet taste that sugars provide.

D-tagatose is a monosaccharide derived from lactose and, more specifically, an epimer of D-fructose. It has been shown to be 90% as sweet as ordinary table sugar while achieving a lower caloric intake. The Food and Drug Administration (FDA) issued a no-objection letter to the claim that D-tagatose effectively yields 1.5 kcal/g, whereas ordinary table sugar contains approximately 4 kcal/g. D-tagatose has also been shown to be safe and efficacious for treating type 2 diabetes. Specifically, D-tagatose has been shown to lower fasting blood glucose levels, HbA1c, LDL, and total cholesterol. In addition, D-tagatose is a known antioxidant and prebiotic. Thus, D-tagatose may provide the desired sweet taste while avoiding the issues associated with more bioavailable sugars.

D-tagatose follows a metabolic pathway identical to fructose, but only 20% of orally ingested D-tagatose is fully metabolized. Furthermore, D-tagatose is also generally recognized as safe (GRAS) by the FDA for use in food and beverages. Additionally, in 2004, the Joint Food and Agriculture Organization/World Health Organization reference expert committee on food additives granted a safe daily intake of D-tagatose as "not specified," meaning it has such low toxicity that it does not need daily intake monitoring. D-tagatose is a healthy and naturally derived alternative to ordinary table sugar for pharmaceuticals and food products, such as gum, where sweetness is desired but harmful side effects such as cariogenicity are not desirable.

Despite D-tagatose's potential advantages over ordinary table sugar, D-tagatose's commercial application has faced setbacks due to the costs of large-scale production. Large-scale D-tagatose production remains costly, as the process often requires multiple purification steps using simulated moving bed chromatography, several lengthy vacuum evaporation steps, and slow processes like continuous crystallization. In an attempt to reduce manufacturing costs, it is proposed in this document to utilize spray-drying unit operation to eliminate the need for continuous crystallization. In particular, D-tagatose processed via continuous crystallization takes on residence times on the order of tens of minutes, while spray-drying generally takes residence times of seconds to minutes.

In brief, spray-drying consists of four key stages: (A) preparation of a feed solution using a solvent or solvent system that can readily dissolve the desired compounds, (B) atomization of the feed solution into the drying chamber containing a hot inert processing gas, (C) evaporation of the droplets to produce solid particles, and (D) separation of the processing gas and the particles via a cyclone and a collection jar placed downstream of the drying chamber as is schematically shown in FIG. 1. A secondary drying process is then required to remove residual solvents down to safe ingestion limits as outlined by governing bodies such as the FDA and the International Council of Harmonization (ICH).

The material properties of D-tagatose (such as its hydrophilic nature and low glass transition temperature) make it challenging to spray-dry. Hydrophilicity makes it challenging to develop an appropriate solvent system for spray-drying because typical feed solutions consist primarily of organic solvents such as acetonitrile, acetone (ACE), ethanol, dimethylformamide, and methanol. Organic solvents often exhibit high volatility in comparison to water as well as lower heat capacity, both of which promote evaporation (and hence particle formation). In practice, the use of water requires higher inlet temperature ($T_{in}$) within the spray-dryer and limits the processing space since the glass transition temperature ($T_g$) of D-tagatose is quite low. The additional energy introduced into the dryer needed to ensure that the high $T_{in}$ is achieved can then result in a decreased efficiency of the overall process as well as an increased outlet temperature ($T_{outlet}$) when all other parameters are held constant. Though the increase in $T_{outlet}$ may be overcome by increasing the liquid feed rate or adjusting the ratio of gas to liquid feed, allowing the $T_{outlet}$ to stay approximately constant with increased $T_{in}$, a balance must be struck between the product $T_g$ and the processing space.

In particular, the glass transition represents the point where the material moves from a rubbery, free-flowing supercooled liquid (i.e., above the $T_g$) to a glassy, rigid state (i.e., below the $T_g$). For D-tagatose, when operating above the $T_g$ of the spray-dried material, the efficiency of the process is dramatically compromised and the material will typically become "sticky" in nature and most often lack particle formation. On the other hand, if the $T_g$ of the spray-dried product is greater than or near the $T_{outlet}$, particles may be harvested much more effectively.

"Stickiness" or operation at an outlet temperature above the $T_g$ of the material produced is a common problem when spray-drying sugars such as fructose, which has similar physicochemical properties to D-tagatose. Stickiness in sugars has been shown to typically occur when the spray-drying temperature is >20° C. higher than the $T_g$. Sugar molecules are thought to have high molecular mobility when operating above the $T_g$. Other factors contributing to stickiness among sugars include high solubility. D-tagatose exhibits a low dry $T_g$ of 18.92° C. typical of simple sugars. These factors place formidable constraints on the available processing space. The presence of residual solvents can depress the $T_g$, exacerbating the product stickiness problem. Thus, D-tagatose is not considered within the processing space of spray-drying using traditional approaches.

One alternative is to formulate D-tagatose with a high molecular weight excipient to raise the $T_{gmix}$ to within processing range. Phase behavior is measured in the systems studied but may not be critical as long as D-tagatose is processable and the amorphous phase or the residual amorphous phase (which may exist if D-tagatose crystallizes) has a $T_g$ that allows for efficient particle collection (i.e., a high yield). So, if and when D-tagatose crystallizes over time, it may not be important because the residual amorphous phase $T_g$ will only increase and the solubility of D-tagatose is very high (the aqueous solubility of crystalline D-tagatose is 160 g/100 mL at 20° C.).

In the work presented in this document, D-tagatose is co-dissolved with a functional polymer excipient having a relatively high $T_g$ to manipulate the material properties of the resulting excipient/D-tagatose composite solid particulates produced. In this manner, D-tagatose is shown to be processible for the first time via spray-drying without compromising the desired sweet taste.

SUMMARY

In accordance with the purposes and benefits set forth herein, a D-tagatose spray-drying feed formulation is provided. That formulation comprises, consists of or consists essentially of a mixture of D-tagatose and a functional polymer excipient co-dissolved in a solvent to produce a excipient/D-tagatose composite having a glass transition temperature of greater than 30° C. In one or more of the many possible embodiments of the formulation, that formulation has a glass transition temperature for the excipient/D-tagatose composite that is between about 30° C. and about 40° C. In one or more of the many possible embodiments of the formulation, that formulation has a glass transition temperature for the excipient/D-tagatose composite that is between about 30° C. and about 35° C.

In one or more of the many possible embodiments of the formulation, the functional excipient may be selected from a group of excipients consisting of an amorphous polymer, a sugar that has an amorphous state hydroxypropylmethylcellulose acetate succinate, polyvinylpyrrolidone K90, D-trehalose, hydroxypropylmethylcellulose, polyvinylpyrrolidone K64, citric acid and combinations thereof.

In one or more of the many possible embodiments of the formulation, the D-tagatose and the functional excipient are provided at a weight ratio of about 1:1.

In one or more of the many possible embodiments of the formulation, the solvent comprises a co-solvent system. That co-solvent system may include acetone and water. The acetone and water may be provided at a ratio of between 1:1 and 4.6:1 (v/v %). In other embodiments, that co-solvent system includes water and methanol, water and propanol or water and ethanol. In still other embodiments a tri-solvent system may be used. One possible tri-solvent system useful for the method is ethanol, methanol and water.

In one useful embodiment of the formulation, the formulation is an about 5% (w/v %) solution of about 1:1 (w/w) ratio of D-tagatose to functional excipient in a co-solvent system of acetone and water provided in an acetone to water ratio of between about 1:1 and about 4.6:1 (v/v %).

In accordance with yet another aspect, a method of spray-drying D-tagatose, comprises, consists of or consists essentially of the steps of: (a) preparing a D-tagatose spray-drying feed formulation from a mixture of D-tagatose and a functional excipient co-dissolved in a solvent to produce a excipient/D-tagatose composite having a glass transition temperature of greater than 30° C., (b) atomizing the D-tagatose spray-drying formulation in a drying chamber containing a hot inert processing gas and evaporating droplets to produce solid particles of D-tagatose and (c) separating and collecting the solid particles of excipient/D-tagatose composite from the processing gas.

In one or more of the many possible embodiments of the method, the method includes the step of co-dissolving the mixture of the D-tagatose and the functional excipient in a co-solvent system including water and acetone.

In one or more of the many possible embodiments of the method, the method includes the step of using an amorphous polymer, a sugar that has an amorphous state, hydroxypropylmethylcellulose acetate succinate, polyvinylpyrrolidone K90, D-trehalose, hydroxypropylmethylcellulose, polyvinylpyrrolidone K64, citric acid or combinations thereof as the functional excipient.

In one or more of the many possible embodiments of the method, the method includes the step of mixing the D-tagatose and the functional excipient at a weight ratio of about 1:1.

In one or more of the many possible embodiments of the method, the method includes the step of providing the acetone and the water at a ratio of between 1:1 and 4.6:1 (v/v %).

In accordance with yet another aspect, a method of spray-drying D-tagatose comprises, consists of or consists essentially of the steps of: (a) spraying, into a drying chamber containing a hot, inert processing gas, a mixture of D-tagatose and a functional excipient co-dissolved in a solvent to produce a polymer/D-tagatose composite having a glass transition temperature of greater than 30° C. and (b) collecting spray-dried particles of excipient/D-tagatose composite.

In one or more of the many possible embodiments of the method, the method includes the step of co-dissolving the mixture of the D-tagatose and the functional excipient in a co-solvent system including water and acetone.

In one or more of the many possible embodiments of the method, the method includes the step of using an amorphous polymer, a sugar that has an amorphous state, hydroxypropylmethylcellulose acetate succinate, polyvinylpyrrolidone K90, D-trehalose, hydroxypropylmethylcellulose, polyvinylpyrrolidone K64, citric acid or combinations thereof as the functional excipient.

In one or more of the many possible embodiments of the method, the method includes the step of mixing the D-tagatose and the functional excipient at a weight ratio of about 1:1.

In one or more of the many possible embodiments of the method, the method includes the step of providing the acetone and the water are provided at a ratio of between 1:1 and 4.6:1 (v/v %).

In the following description, there are shown and described several preferred embodiments of the D-tagatose spray-drying feed formulation and method of spray-drying D-tagatose. As it should be realized, the formulation and method are capable of other, different embodiments and their several details are capable of modification in various, obvious aspects all without departing from the formulation and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the patent specification, illustrate several aspects of the D-tagatose spray-drying feed formulation and method of spray-drying D-tagatose and together with the description serve to explain certain principles thereof.

Figure 1:
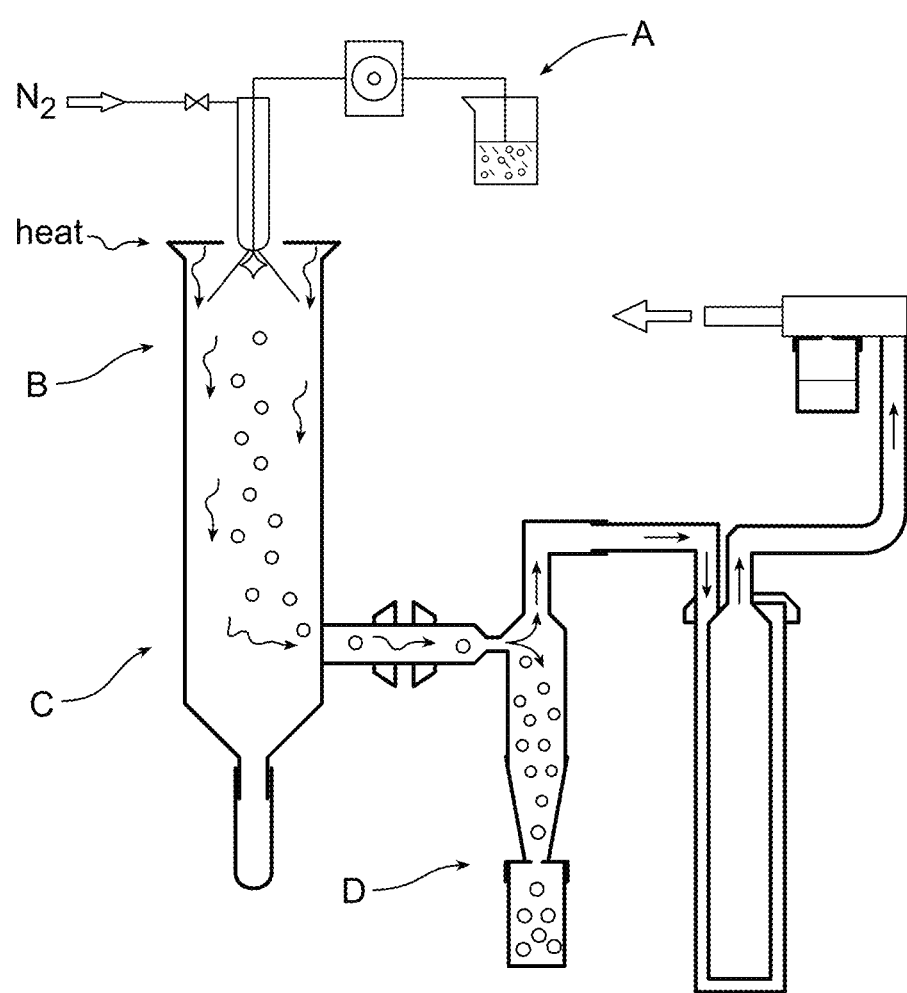
FIG. 1 is a schematic illustration of the D-tagatose spray-drying process.
Figure 2:
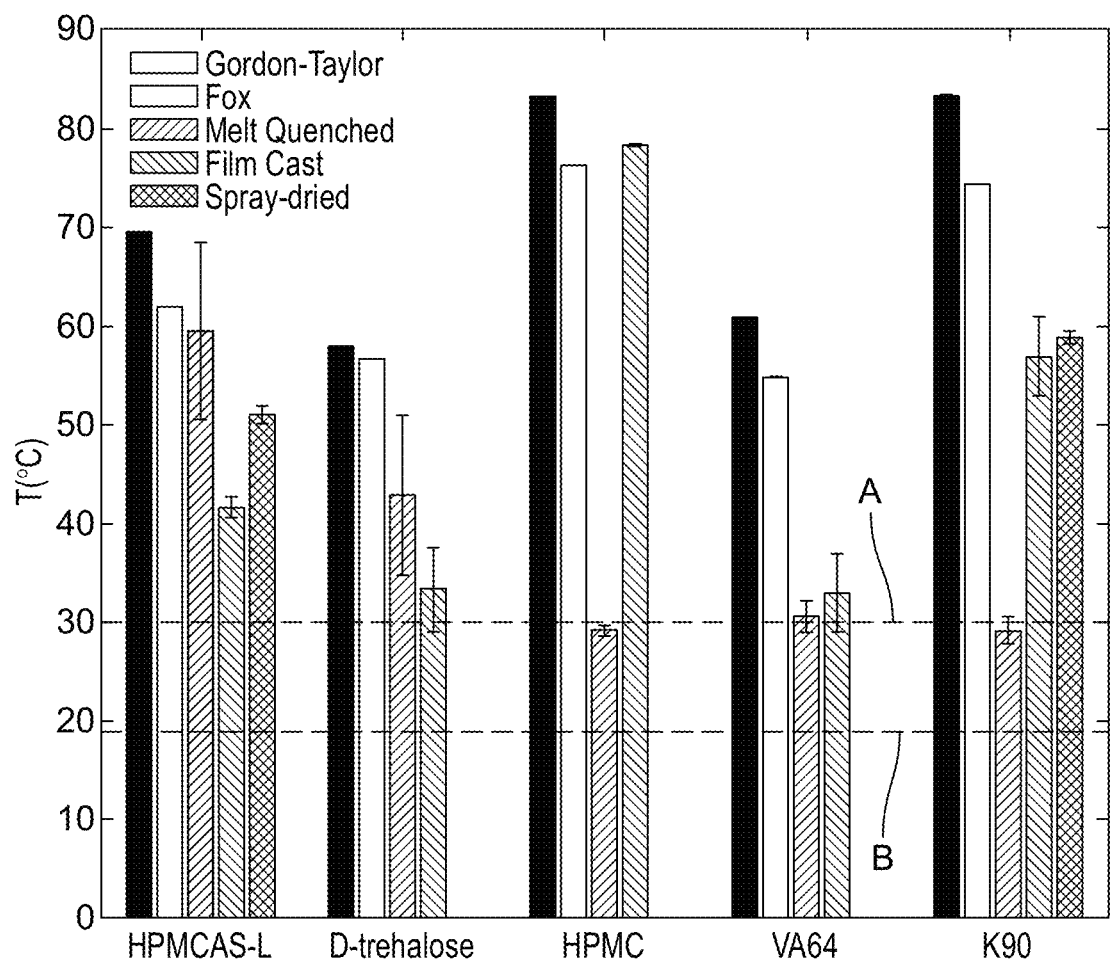
FIG. 2 is a graphic comparison of theoretical and experimentally determined glass transition temperatures ($T_g$) of 1:1 (w/w) D-tagatose to excipient mixtures.
Figure 3:
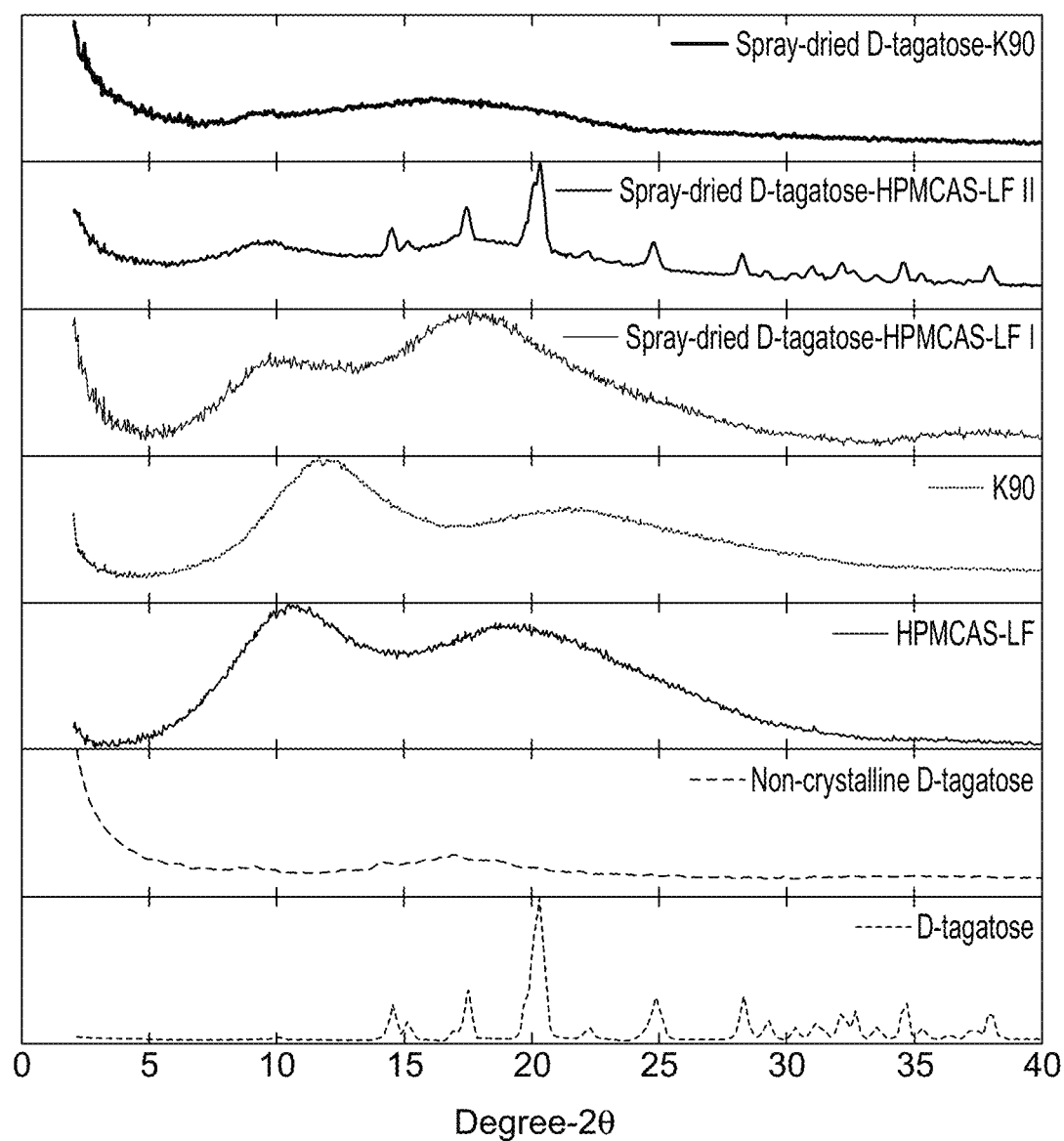
FIG. 3 illustrate PXRD diffractograms of spray-dried polyvinylpyrrolidone K90/D-tagatose composite particles, spray-dried hydroxypropylmethylcellulose acetate succinate/D-tagatose composite particles, polyvinylpyrrolidone K90 particles, hydroxypropylmethylcellulose acetate succinate particles, non-crystalline D-tagatose particles, and D-tagatose particles.
Figure 4:
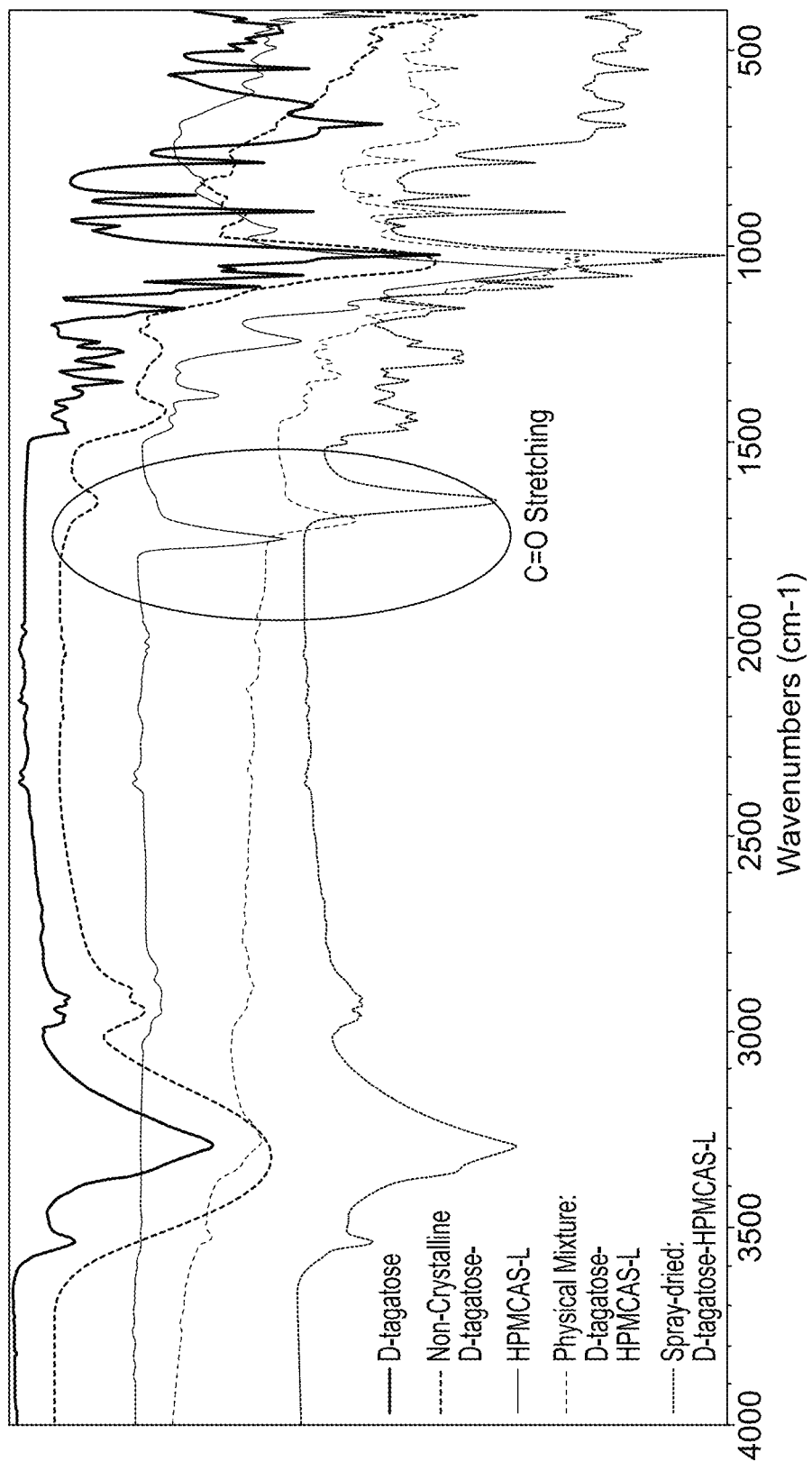
FIG. 4 illustrates ATR-FTIR spectra of D-tagatose, hydroxypropylmethylcellulose acetate succinate, hydroxypropylmethylcellulose acetate succinate/D-tagatose physical mixture (1:1 w/w) and spray-dried hydroxypropylmethylcellulose acetate succinate/D-tagatose (1:1 w/w).
Figure 5:
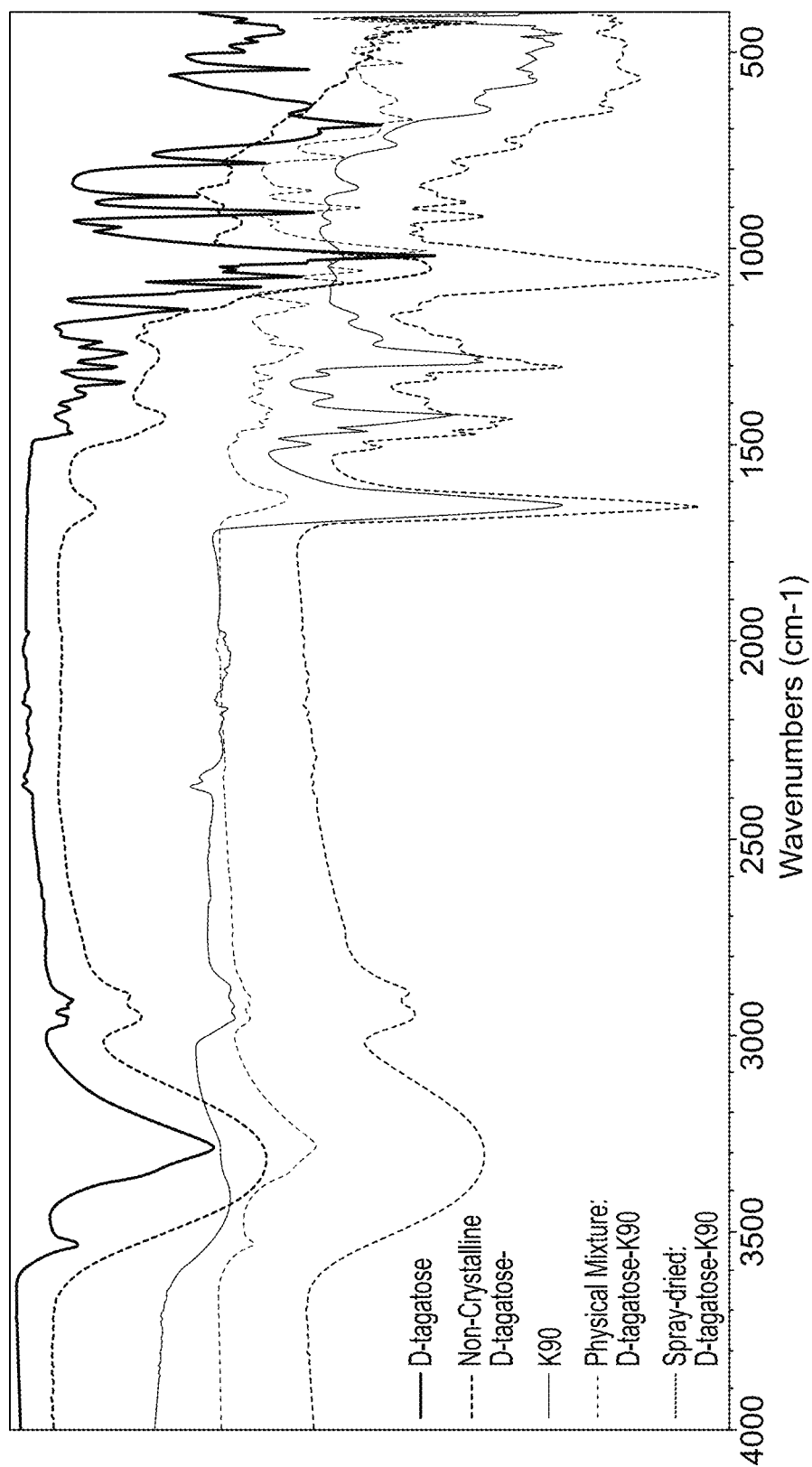
FIG. 5 illustrates ATR-FTIR spectra of D-tagatose, polyvinylpyrrolidone K90, polyvinylpyrrolidone K90/D-tagatose mixture (1:1 w/w) and spray-dried polyvinylpyrrolidone K90/D-tagatose (1:1 w/w).
Figure 6:
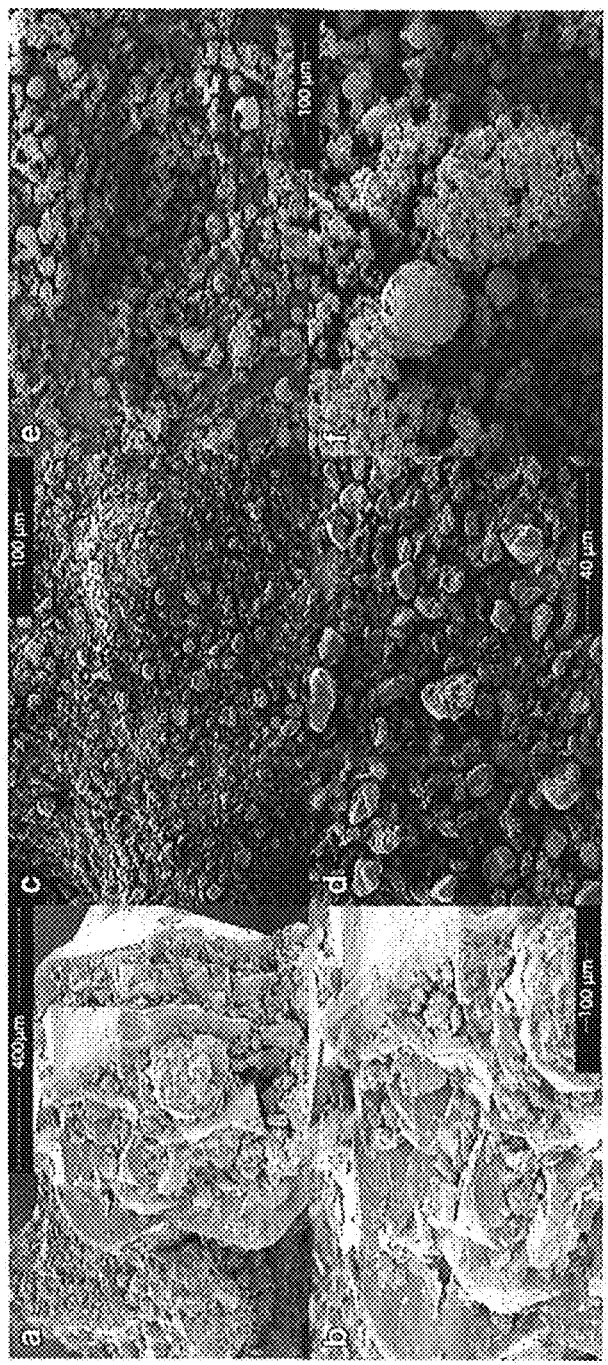
FIG. 6 is representative SEM images of (a, b) D-tagatose crystalline, (c, d) hydroxypropylmethylcellulose acetate succinate and (e, f) spray-dried hydroxypropylmethylcellulose acetate succinate/D-tagatose.
Figure 7:
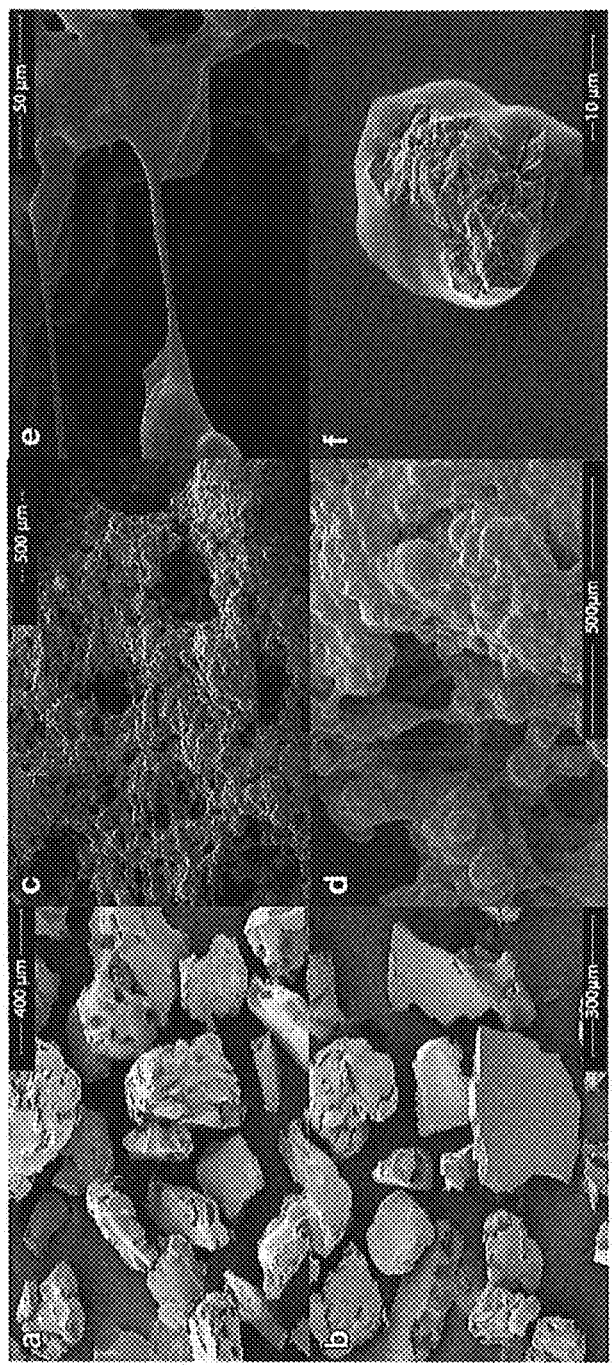
FIG. 7 is representative SEM images of (a, b) polyvinylpyrrolidone K90 and (c-f) spray-dried polyvinylpyrrolidone K90/D-tagatose.

Reference will now be made in detail to the present preferred embodiments of D-tagatose spray-drying feed formulation and method of spray-drying D-tagatose, examples of which are illustrated in the accompanying drawing figures.

DETAILED DESCRIPTION

A D-tagatose spray-drying feed formulation comprises a mixture of D-tagatose and a functional polymer excipient co-dissolved in a solvent to produce a excipient/D-tagatose composite having a glass transition temperature of greater than 30° C. In some embodiments, the glass transition temperature is greater than 40° C. In still other embodiments, the glass transition temperature is greater than 50° C.

The functional excipient may be selected from a group of excipients consisting of an amorphous polymer, a sugar that has an amorphous state, hydroxypropylmethylcellulose acetate succinate (including grades L, M and H), polyvinylpyrrolidone K90, D-trehalose, hydroxypropylmethylcellulose, polyvinylpyrrolidone K64, citric acid and combinations thereof.

The D-tagatose and the functional excipient are provided at substantially any weight ratio suitable for the intended purpose including, for example, at a weight ratio of about 1:1.

The solvent used in the spray-drying feed formulation may be substantially any solvent suitable for the intended purpose including, for example, an appropriate co-solvent system. That co-solvent system may include acetone and water. The acetone and water may be provided at a ratio of between 1:1 and 4.6:1 (v/v %). In other embodiments, the co-solvent system may include methanol and water, propanol and water or ethanol and water. See Table 1 below.

TABLE 1

Summarizes weight percentage (w %) of varying water: organic dual solvent systems. w % of D-tagatose is fully dissolved.

|  | w % Tagatose | ± | w % water | ± | w % Organic | ± |
| --- | --- | --- | --- | --- | --- | --- |
| Methanol | 11.2 | 0.403 | 46.0 | 0.209 | 42.7 | 0.392 |
| Ethanol | 11.6 | 0.412 | 45.9 | 0.413 | 42.5 | 0.198 |
| 2-Propanol | 11.1 | 0.400 | 45.6 | 0.208 | 43.3 | 0.394 |
| Acetone | 11.3 | 0.025 | 46.0 | 0.246 | 42.7 | 0.246 |

Tri-solvent systems may also be used. One example of a tri-solvent system is ethanol, methanol and water. See Table 2 below.

TABLE 2

Summarizes tri-solvent systems that have shown to dissolve D-tagatose. With the preferred (maximum organic (minimized water—does not perform as well in spray-drying as organic solvents) highlighted in the box.

Mixture of ethanol, methanol and water

| Ethanol (mL) | w % Tagatose | w % water | w % Organic | Methanol (mL) | w % Tagatose | w % water | w % Organic |
| --- | --- | --- | --- | --- | --- | --- | --- |
| 1 | 10.887 | 37.324 | 51.789 | 1 | 10.830 | 39.808 | 49.3620231 |
| 2 | 9.999 | 36.185 | 53.816 | 2 | 9.292 | 37.459 | 52.8123019 |
| 3 | 9.292 | 32.436 | 58.272 | 3 | 8.704 | 35.506 | 55.7893055 |
| *5 mL Methanol | | | | 5 mL Methanol | | | |

In one particularly useful embodiment, the D-tagatose spray-drying formulation is about 5% (w/v %) solution of about 1:1 (w/w) ratio of D-tagatose to functional excipient in a co-solvent system of acetone and water provided in an acetone to water ratio of between about 1:1 and about 4.6:1 (v/v %).

The D-tagatose spray-drying formulation described above and throughout this document is useful in a method of spray-drying D-tagatose. That method may be described as comprising the steps of: (a) preparing a D-tagatose spray-drying feed formulation from a mixture of D-tagatose and a functional excipient co-dissolved in a solvent to produce a excipient/D-tagatose composite having a glass transition temperature of greater than 30° C., (b) atomizing the D-tagatose spray-drying formulation in a drying chamber containing a hot inert processing gas (such as nitrogen argon) and evaporating droplets to produce solid particles of D-tagatose and (c) separating and collecting the solid particles of excipient/D-tagatose composite from the processing gas.

The method may include the additional step of co-dissolving the mixture of the D-tagatose and the functional excipient in a co-solvent system including water and acetone, water and methanol, water and propanol, or water and ethanol. The method may include the additional step of using and amorphous polymer, a sugar that has an amorphous state, hydroxypropylmethylcellulose acetate succinate, polyvinylpyrrolidone K90, D-trehalose, hydroxypropylmethylcellulose, polyvinylpyrrolidone K64, citric acid or combinations thereof as the functional excipient.

The method may include the step of mixing the D-tagatose and the functional excipient at a weight ratio of about 1:1 or any other weight ratio appropriate for the intended purpose of spray-drying. The method may also include the step of providing the acetone and the water at a ratio of between 1:1 and 4.6:1 (v/v %).

The method of spray-drying D-tagatose may also be characterized as comprising the steps of: (a) spraying, into a drying chamber containing a hot, inert processing gas, a mixture of D-tagatose and a functional excipient co-dissolved in a solvent to produce a excipient/D-tagatose composite having a glass transition temperature of greater than 30° C. and (b) collecting spray-dried particles of excipient/D-tagatose composite.

Such a method may include the step of co-dissolving the mixture of the D-tagatose and the functional excipient in a co-solvent system including water and acetone, water and methanol, water and propanol or water and ethanol. Such a method may include the step of using an amorphous polymer, a sugar that has an amorphous state, hydroxypropylmethylcellulose acetate succinate, polyvinylpyrrolidone K90, D-trehalose, hydroxypropylmethylcellulose, polyvinylpyrrolidone K64, citric acid or combinations thereof as the functional excipient. Of course, other excipients could be used so long as they are appropriate for spray-drying excipient/D-tagatose composite particles.

The method may include the step of mixing the D-tagatose and the functional excipient at a weight ratio of about 1:1 or any other appropriate weight ratio. The method may include the step of providing the acetone and the water are provided at a ratio of between 1:1 and 4.6:1 (v/v %).

Experimental

Materials

D-(−)-tagatose (MW: 180.16) was a gift from Biospherics.net (Wilmington, DE). Polyvinylpyrrolidone-co-vinyl acetate (VA64) was purchased from BASF Corporation (Florham Park, NJ, USA) as Kollidon VA64. Polyvinylpyrrolidone was purchased from BASF Corporation as Kollidon K90F (K90). Hydroxypropylmethylcellulose acetate succinate (HPMCAS-LF) was a gift from Ashland Global Specialty Chemicals Inc. as Aqua Solve.

D-(+)-trehalose, dihydrate molecular biology grade, was acquired from Life Science (St. Petersburg, FL). Hydroxypropylmethylcellulose (HPMC) was obtained from Colorcon as Methocel. T-Zero hermetic aluminum pans and lids for differential scanning calorimetry (DSC) experiments were purchased from TA Instruments (New Castle, DE). HiPerSolv chromanorm acetone (ACE) and HPLC grade ethanol were purchased from VWR International (Radnor, PA). Milli-Q double-distilled water was obtained in house via a Millipore MilliPak 40 Q-Pod.

Methods and Sample Preparation Determination of the Glass Transition Temperatures $T_g$ of Melt-Quenched Samples Glass transition temperatures were determined using DSC for physical mixtures of D-tagatose and respective excipients subjected to melt quenching. Samples were prepared by geometrically mixing D-tagatose and excipients at a 1:1 (w/w) ratio. Once mixed, the samples were then rigorously ground using a mortar and pestle before being hermetically sealed within a T-Zero pan. Once sealed, the samples were transferred to a Q2000 DSC (TA Instruments, New Castle, DE). All samples were run with the DSC operating in the modulation mode with a "pinhole" lid to better capture the sample's behavior instead of any residual vapors. The modulating method was first equilibrated at −20° C. before heating at 10° C./min to 140° C. (Note: this heating rate was chosen with care to avoid decomposition of D-tagatose. Sugars such as fructose have been shown to decompose before melting when slow rates of heating are used, while decomposition starts just after melting at a fast rate of heating [14]. Samples were held at 140° C. for 1 min before cooling at 20° C./min to −10° C. to reduce potential degradation of D-tagatose, which degrades around its melting temperature between 135 and 140° C.). Once −10° C. was reached, samples were set to modulate at ±0.5° C. every 60 s immediately and held for 5 min before ramping 1° C./min back to 140° C. Reported $T_g$ values were averages of triplicate samples, each determined from the midpoint of the glass transition step change from the resultant reversible heat flow curves vs. temperature thermograms. All DSC mass samples were between 1 and 5 mg.

$T_g$ Determination of Solvent Cast Films

Glass transition temperature was determined for solvent-casted film samples of D-tagatose with individual excipients via DSC using the method described in the "$T_g$ of Melt-Quenched Samples" section. Films were prepared by weighing D-tagatose and excipients at a 1:1 (w/w) ratio before being dissolved in 20-mL glass vials containing 10 mL of ACE and 10 mL of Milli-Q water to create a 5% (w/v) suspension. Solutions were then created by sonicating the 20-mL suspension at 25° C. for approximately 10 min. Once solutions were prepared, they were placed in a petri dish of 67.9 mm in diameter and placed under vacuum at 60° C. for ~ 24 h. It should be noted that this method did not create a solution for D-tagatose with HPMCAS-L or HPMC. Instead, D-tagatose with HPMCAS-L was dissolved in 14.08 mL ACE to 5.91 mL of Milli-Q water [38]. HPMC, however, is poorly soluble in ACE, and after similar attempts, an ethanol-water solvent system was used instead.

Theoretical $T_g$ Determination

Theoretical $T_g$ values for mixtures were calculated via the Gordon-Taylor and Fox equations, as is shown by Eqs. (1) and (2) respectively.

In another experiment, 3 grams of D-tagatose was dissolved in a tri-solvent system of methanol:ethanol:water—15 mL:9 mL:11.1 mL, producing a 9% D-tagatose solution. The collection chamber did produce a sticky product. In further experiments, the drug-loading of the solution was lowered all the way to a 3% D-tagatose solution. These attempts did produce higher yield and slightly drier powder.

The settings on the dryer during these sprays were a mixture of the numbers provided in Table 3.

TABLE 3

Summarizes Procept Spray-Drying Parameters during spraying D-tagatose with methanol:ethanol:water solvent systems.

| Inlet temperature (C.) | Inlet gas rate (m3/min) |
| --- | --- |
| 75 | |
| 70 | |
| 65 | 0.40 |
| 50 | 0.5 |

*Pump speed 85 rpm, Nozzle Gas Pressure 0.45 mbar, cyclone differential 35 mbar

In another experiment, a dry powder of D-tagatose was sprayed with methanol:ethanol:water at 5 mL:3 mL:3.5 mL at a 5% by weight D-tagatose loading (~0.52 grams dissolved) with the following spray-dry settings:

Inlet temperature: 120° C.
Inlet gas flow: 0.40 m3/min
Atomization pressure: 3 bar
Cyclone differential: 40 mbar
Outlet temperature: 57.9° C.

Also both the Buchi and Procept dryer was equipped with a bi-fluid nozzle. It is believed that a tri-fluid nozzle could improve solvent ratios when spray-drying D-tagatose.

Ranges for solvents useful in this method are:

Acetone:Water
  5 mL:4.1 mL—~1 gram D-tagatose. Here you can keep adding water and it will continue to dissolve D-tagatose.
Ethanol:Water
  5 mL:4.2 mL—~1 gram D-tagatose. Here you can keep adding water and it will continue to dissolve D-tagatose.
Methanol:Water
  5 mL:3.1 mL—~1 gram D-tagatose. Here you can keep adding water and it will continue to dissolve D-tagatose.
2-Propanol:Water
  5 mL:3.6 mL—~1 gram D-tagatose. Here you can keep adding water and it will continue to dissolve D-tagatose.
Methanol:Ethanol:Water
  5 mL:1 mL:3.4 mL—~1 gram D-tagatose. Here you can keep adding water and it will continue to dissolve D-tagatose.
2-Propanol:Ethanol:Water
  5 mL:1 mL:4.6 mL—~1 gram D-tagatose. Here you can keep adding water and it will continue to dissolve D-tagatose. *Sonicate while adding water.
2-Propanol:Ethanol:Water
  1 mL:5 mL:4.2 mL—~1 gram D-tagatose. Here you can keep adding water and it will continue to dissolve D-tagatose. *Sonicate while adding water.
2-Propanol:Acetone:Water
  5 mL:1 mL:3.6 mL—~1 gram D-tagatose. Here you can keep adding water and it will continue to dissolve D-tagatose. *Sonicate while adding water.
2-Propanol:Acetone:Water
  1 mL:5 mL:3.8 mL—~1 gram D-tagatose. Here you can keep adding water and it will continue to dissolve D-tagatose. *Sonicate while adding water.

The following steps outline the spray-drying of D-tagatose using hydroxyproplymethylcellulose acetate succinate (HPMCAS).

Solution Prep
  1. Mix acetone and water keeping a 5 mL:1.1 mL (ACE:H20) ratio.
  2. Geometrically mix D-tagatose and HPMCAS
  3. Pour the geometrically mixed D-tagatose and HPMCAS into the Acetone:Water solution.
  4. Sonicate ~5 minutes
  5. At this point you should have a solution of D-tagatose for spray-drying.

Spray Instructions
  6. Spray-dryer should be turned on and thermally equilibrated. This can be done by setting the dryers inlet temperature to the desired degree before spraying at least a 100 mL (on laboratory scale dryer) solution of solvent system to be used. Solvent system should be ABSENT of D-tagatose at this time. That is if spraying D-tagatose with Acetone:Water system. At this stage you should spray 100 mL of Acetone:Water solution—at desired ratio- to allow the spray-dryer to thermally equilibrate the inlet temperature.
  7. After thermal equilibration is complete (dryers inlet temperature is not fluctuating more then 1 or 2 degrees) quickly insert D-tagatose loaded solution.
  8. Allow time for spraying.
  9. Collect from collection jar.

The following steps outline the spray drying of D-tagatose using polyvinylpyrrolidone (PVP) K90.

Solution Prep
  1. Mix acetone and water keeping a 5 mL:1.1 mL (ACE:H20) ratio.
  2. Geometrically mix D-tagatose and PVPK90
  3. Pour the geometrically mixed D-tagatose and HPMCAS into the Acetone:Water solution.
  4. Sonicate ~5 minutes
  5. At this point you should have a solution of D-tagatose for spray-drying.

Spray Instructions
  6. Spray-dryer should be turned on and thermally equilibrated. This can be done by setting the dryers inlet temperature to the desired degree before spraying at least a 100 mL (on laboratory scale dryer) solution of solvent system to be used. Solvent system should be ABSENT of D-tagatose at this time. That is if spraying D-tagatose with Acetone:Water system. At this stage you should spray 100 mL of Acetone:Water solution—at desired ratio- to allow the spray-dryer to thermally equilibrate the inlet temperature.
  7. After thermal equilibration is complete (dryers inlet temperature is not fluctuating more then 1 or 2 degrees) quickly insert D-tagatose loaded solution.
  8. Allow time for spraying.
  9. Collect from collection jar.

The following steps outline the spray drying of D-tagatose using a tri-solvent system.

Solution Prep
  1. Mix methanol, ethanol, and water together keeping the 15 mL:9 mL:11.1 mL ratio. Assuming this ratio for the remainder of instructions.
  2. Add 3 grams of D-tagatose
  3. Sonicate for ~5-10 minutes 4. At this point you should have a solution of D-tagatose for spray-drying.

Spray Instructions

5. Spray-dryer should be turned on and thermally equilibrated. This can be done by setting the dryers inlet temperature to the desired degree before spraying at least a 100 mL (on laboratory scale dryer) solution of solvent system to be used. Solvent system should be ABSENT of D-tagatose at this time. That is if spraying D-tagatose with Methanol:Ethanol:Water system. At this stage you should spray 100 mL of the Methanol:Ethanol:Water solution—at desired ratio- to allow the spray-dryer to thermally equilibrate the inlet temperature. ~120 C
6. After thermal equilibration is complete (dryers inlet temperature is not fluctuating more then 1 or 2 degrees) quickly insert D-tagatose loaded solution.
7. Allow time for spraying.
8. Collect from collection jar.

The following steps outline the spray-drying of D-tagatose using polyvinylpyrrolidone K64 (PVPK64).

Solution Prep

1. Add 30 mL Milli-Q water
2. Add 3 grams of D-tagatose
3. Add 50 mL Acetone
4. Sonicate for ~2 minutes
5. Add 30 mL Ethanol
6. Sonicate for ~2 minutes
7. Add 1.285 grams of PVPK64
8. Sonicate and mix until dissolved
9. At this point you should have a solution of D-tagatose for spray-drying.

Spray Instructions

1. Spray-dryer should be turned on and thermally equilibrated. This can be done by setting the dryers inlet temperature to the desired degree before spraying at least a 100 mL (on laboratory scale dryer) solution of solvent system to be used. Solvent system should be ABSENT of D-tagatose at this time. That is if spraying D-tagatose with Acetone:Ethanol:Water system. At this stage you should spray 100 mL of the Acetone:Ethanol:Water solution—at desired ratio- to allow the spray-dryer to thermally equilibrate the inlet temperature. Inlet temperature ~70 C
2. After thermal equilibration is complete (dryers inlet temperature is not fluctuating more then 1 or 2 degrees) quickly insert D-tagatose loaded solution.
3. Allow time for spraying.
4. Collect from collection jar.

The following steps outline the spray-drying of D-tagatose using citric acid (CA).

Solution Prep

1. Add D-tagatose with CA at a 7:3 (tag:CA) ratio.
2. Add ~151 mg of this mix to 50 mL ethanol
3. Add ~5 mL water
4. Sonicate until dissolved
5. At this point you should have a solution of D-tagatose for spray-drying.

Spray Instructions

1. Spray-dryer should be turned on and thermally equilibrated. This can be done by setting the dryers inlet temperature to the desired degree before spraying at least a 100 mL (on laboratory scale dryer) solution of solvent system to be used. Solvent system should be ABSENT of D-tagatose at this time. That is if spraying D-tagatose with Ethanol:Water system. At this stage you should spray 100 mL of the Ethanol:Water solution—at desired ratio- to allow the spray-dryer to thermally equilibrate the inlet temperature. Inlet temperature ~80 C Buchi spray-dry parameter—50% pump speed and 50% nitrogen flow.
2. After thermal equilibration is complete (dryers inlet temperature is not fluctuating more then 1 or 2 degrees) quickly insert D-tagatose loaded solution.
3. Allow time for spraying.
4. Collect from collection jar.

Each of the following terms written in singular grammatical form: "a", "an", and "the", as used herein, means "at least one", or "one or more". Use of the phrase "One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a functional excipient", and "a step or procedure", as used herein, may also refer to, and encompass, a plurality of functional excipients and a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

The phrase "consisting of", as used herein, is closed-ended and excludes any element, step, or ingredient not specifically mentioned. The phrase "consisting essentially of", as used herein, is a semi-closed term indicating that an item is limited to the components specified and those that do not materially affect the basic and novel characteristic(s) of what is specified.

Terms of approximation, such as the terms about, substantially, approximately, etc., as used herein, refers to ±10% of the stated numerical value.

It is to be fully understood that certain aspects, characteristics, and features of the D-tagatose spray-drying feed formulation and method of spray-drying D-tagatose, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the D-tagatose spray-drying feed formulation and method of spray-drying D-tagatose which are illustratively described and presented in combination or sub-combination in the context or format of a single embodiment may also be illustratively described and presented in the context or format of a plurality of separate embodiments.

Although the D-tagatose spray-drying feed formulation and method of spray-drying D-tagatose of this disclosure have been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The foregoing has been presented for purposes of illustration and description. It is not intended to be exhaustive or to limit the embodiments to the precise form disclosed.

Obvious modifications and variations are possible in light of the above teachings. All such modifications and variations are within the scope of the appended claims when interpreted in accordance with the breadth to which they are fairly, legally and equitably entitled.

What is claimed:

1. A method of spray-drying D-tagatose, comprising:
preparing a D-tagatose spray-drying feed formulation consisting of a mixture of D-tagatose and a functional polymer excipient co-dissolved in a solvent to produce a functional polymer excipient/D-tagatose composite having a glass transition temperature of greater than 30° C.;
atomizing the D-tagatose spray-drying formulation in a drying chamber containing an inert processing gas and evaporating droplets to produce solid particles of D-tagatose; and
separating and collecting the solid particles of the functional polymer excipient/D-tagatose composite from the processing gas.

2. The method of claim 1, wherein the solvent includes water and acetone, water and methanol, water and propanol, or water and ethanol.

3. The method of claim 2, wherein using an amorphous polymer, a sugar that has an amorphous state, hydroxypropylmethylcellulose acetate succinate, polyvinylpyrrolidone, D-trehalose, hydroxypropylmethylcellulose, polyvinylpyrrolidone, citric acid or combinations thereof is used as the functional polymer excipient.

4. The method of claim 3, wherein the D-tagatose and the functional polymer excipient are mixed at a weight ratio of about 1:1.

5. The method of claim 4, wherein the acetone and the water are provided at a volume ratio of between 1:1 and 4.6:1.

6. A method of spray-drying D-tagatose, comprising:
spraying a mixture consisting of D-tagatose and a functional polymer excipient co-dissolved in a solvent to produce a functional polymer excipient/D-tagatose composite having a glass transition temperature of greater than 30° C. into a drying chamber containing an inert processing gas; and
collecting spray-dried particles of the functional polymer excipient/D-tagatose composite.

7. The method of claim 6, wherein the solvent includes water and acetone, water and methanol, water and propanol, or water and ethanol.

8. The method of claim 7, wherein an amorphous polymer, a sugar that has an amorphous state, hydroxypropylmethylcellulose acetate succinate, polyvinylpyrrolidone, D-trehalose, hydroxypropylmethylcellulose, polyvinylpyrrolidone, citric acid or combinations thereof is used as the functional polymer excipient.

9. The method of claim 8, including mixing the D-tagatose and the functional polymer excipient at a weight ratio of about 1:1.

10. The method of claim 9, including providing the acetone and the water are provided at a volume ratio of between 1:1 and 4.6:1.

* * * * *